United States Patent [19]
Fray et al.

[11] Patent Number: 5,192,404
[45] Date of Patent: Mar. 9, 1993

[54] METHOD FOR MEASURING A MINOR ELEMENT IN A MOLTEN METAL

[75] Inventors: Derek J. Fray; Ramachandran V. Kumar, both of Cambridge, United Kingdom

[73] Assignee: Mineral Industry Research Organisation, London, United Kingdom

[21] Appl. No.: 762,076

[22] Filed: Sep. 18, 1991

Related U.S. Application Data

[62] Division of Ser. No. 417,764, Oct. 6, 1989, abandoned.

[30] Foreign Application Priority Data

Oct. 6, 1988 [GB] United Kingdom ............... 8823507

[51] Int. Cl.$^5$ ......................................... G01N 27/411
[52] U.S. Cl. ........................... 204/153.19; 204/153.1; 204/419; 204/422
[58] Field of Search ............... 204/416, 419, 421–429, 204/153.1, 153.19

[56] References Cited

U.S. PATENT DOCUMENTS

| | | | |
|---|---|---|---|
| 4,166,009 | 8/1979 | Frat | 204/422 |
| 4,174,258 | 11/1979 | Bode | 204/424 |
| 4,377,460 | 3/1983 | Hirayama et al. | 204/428 |
| 4,406,754 | 9/1983 | Narita et al. | 204/424 |
| 4,427,525 | 1/1984 | Lin et al. | 204/424 |
| 4,645,571 | 2/1987 | Dubreuil et al. | 204/422 |
| 4,828,671 | 5/1989 | Lin et al. | 204/424 |
| 4,842,698 | 6/1989 | Kirchnerova et al. | 204/421 |
| 4,855,034 | 8/1989 | Sugimoto et al. | 204/424 |

FOREIGN PATENT DOCUMENTS

| | | |
|---|---|---|
| 0087322A1 | 8/1983 | European Pat. Off. . |
| 0208072 | 3/1987 | European Pat. Off. . |
| 1470558 | 4/1977 | United Kingdom . |
| 1602564 | 11/1981 | United Kingdom . |
| 2097538 | 11/1982 | United Kingdom . |
| WO84/03149 | 8/1984 | World Int. Prop. O. . |

Primary Examiner—T. Tung
Attorney, Agent, or Firm—Jacobson, Price, Holman & Stern

[57] ABSTRACT

A method for the detection and measurement of a minor element in a molten metal, the minor element being selected from the group of phosphorous, silicon, arsenic, antimony and sulfur, includes providing a first electrical lead (5) and immersing it in the molten metal (6), disposing a solid electrolyte matrix (2) in the molten metal in spaced relationship to the first electrical lead, providing a second electrical lead (3) connected to the solid electrolyte matrix (2) so that the matrix is between and separates the leads when the matrix is disposed in the molten metal, and connecting a voltmeter (7) between the other ends of the electrical leads and measuring the EMF between the leads as an indication of the concentration of the minor element in the molten metal. The solid electrolyte is a matrix (2) of alumina selected from the group consisting of $\beta$-alumina and $\alpha + \beta$ alumina and includes a compound of the element to be detected and measured, oxygen, and an element from the group consisting of alkali and alkaline earth metal elements. The elements are chemically combined with the oxygen and the compound dissociates into its constitute elements under the conditions of measurement in the molten metal. The solid electrolyte matrix may be in the form of a closed end of a tubular member (1).

7 Claims, 6 Drawing Sheets

Emf versus logarithm of ppm phosphorus

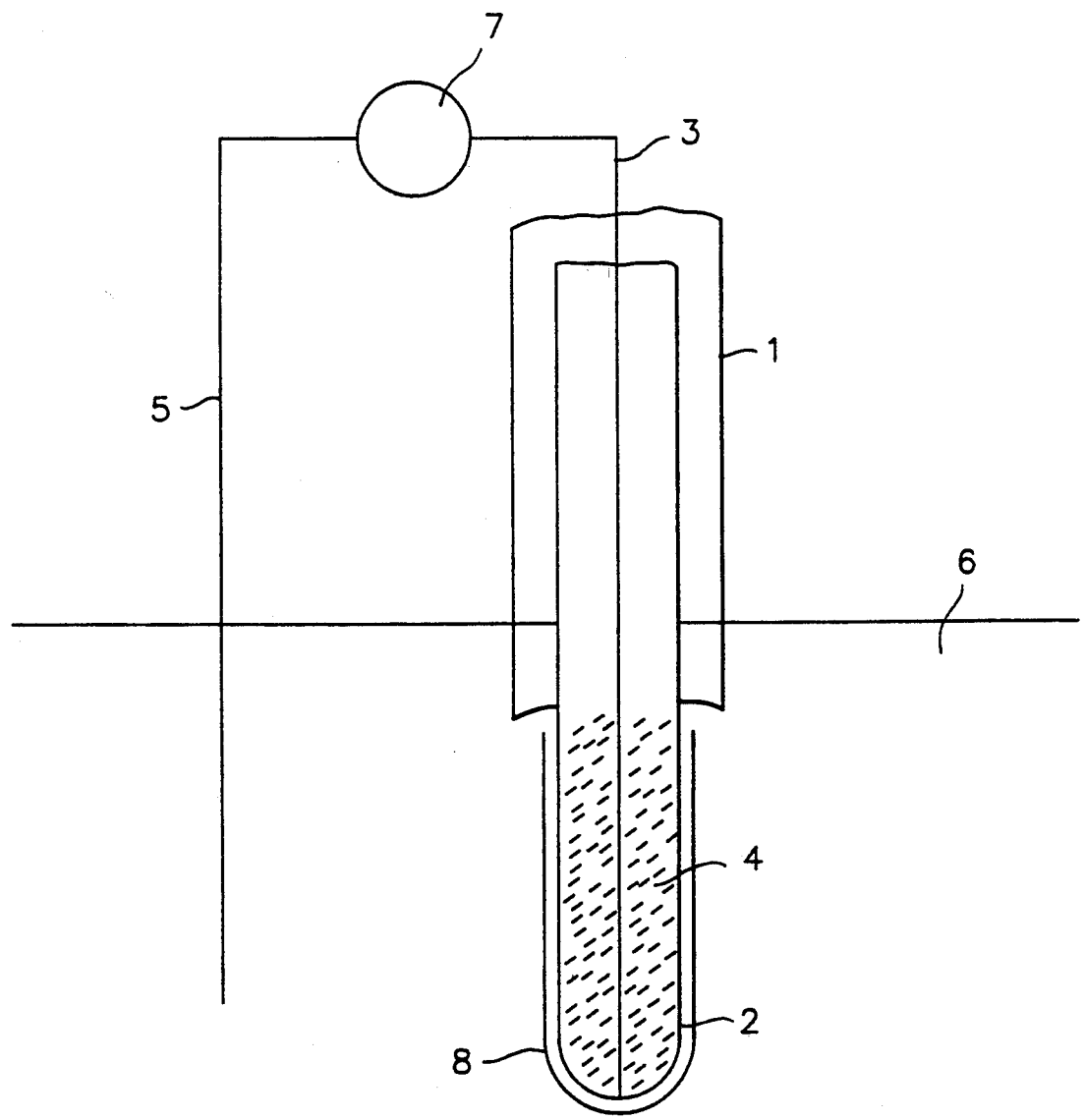

METHOD FOR MEASURING A MINOR ELEMENT IN A MOLTEN METAL

This application is a division of application Ser. No. 07/417,764, filed Oct. 6, 1989, now abandoned.

BACKGROUND OF THE INVENTION

This invention relates to a method for the detection and measurement of concentrations for minor elements, especially non-metallic and semi-metallic elements, in molten metallurgical phases, e.g. metals, alloys, slags, matters and drosses.

There is a need, especially in metal refining and alloying processes, for a method to monitor the concentrations of minor elements in the melts as the process proceeds, so that the process can be controlled.

UK patent Nos. GB-A-1,470,558 (corresponding to U.S. Pat. No. 4,166,009) and 1,602,564 describe and claim electrolytic sensors for such purposes, wherein a solid electrolyte, based on a $\beta$-alumina matrix, is interposed between the melt being tested and the elements to be detected or measured. However, the ionic species which can be measured by this prior method are limited to ions which are mobile in the solid electrolyte, i.e. monovalent and some divalent and trivalent ions such as alkali metal/alkaline earth metal ions.

There is a problem where detection or measurement of multi-valent elements such as P, As, Sb, S or Si in metallurgical phases is required, as it may be in many refining or alloying processes.

The present invention therefore seeks to meet this requirement and provide a method which overcomes the disadvantages of the prior art.

BRIEF SUMMARY OF THE INVENTION

The present invention provides a method for the detection and measurement of polyvalent minor elements in molten metallurgical phases, comprising using two electrodes separated by a solid electrolyte matrix on which is deposited a compound comprising the element to be detected and an element whose ions are mobile in the solid electrolyte matrix.

Preferably the solid electrolyte (and the deposition phase) is oxidic in character. More preferably the solid electrolyte is based on $\beta$-alumina or $\alpha + \beta$ alumina.

The element to be detected will normally be a polyvalent non-metallic or semi-metallic element, e.g. phosphorus, silicon, arsenic, antimony or sulphur; while the mobile element will normally be a monovalent or divalent element, e.g. an alkali or alkaline-earth element ion such as Na, Li, K or Ca.

It may also be necessary to deposit with the deposition phase a conducting phase, e.g. a metal, oxide or carbide, which is electrically conducting. Metals in particular may be used as conducting phases and precious metals may be especially useful.

The solid electrolyte is suitably used either in the form of a closed-end tube or is sealed into a silica tube. The reference material (which is usually a mixture of ferric oxide and a metal ferrite) is placed in the tube and the deposition and conducting phases are coated on the external surface of the solid electrolyte.

Thus, in a typical example, the conducting and deposition phases may be platinum/sodium phosphate which may be vapor-deposited on a solid electrolyte matrix which contains sodium ions. In such an example, the platinum acts as an electrical conductor between the solid electrolyte ($\beta$-alumina) and the molten metal. On the surface of the electrolyte the following equilibrium is set up between dissolved Na, P and O in the molten metal or alloy and the solid $Na_3PO_4$.

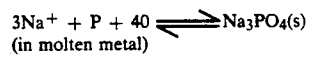
(in molten metal)

If the oxygen content of the metal remains constant (as it usually does by virtue of the metal/metal oxide equilibrium) any change in phosphorus content results in a change in the sodium activity in the solid $Na_3PO_4$ and this is detected by the $\beta$-alumina sensor. In this way phosphorus can be detected in melts based on aluminum, tin or cooper. A similar approach can be used to detect other polyvalent elements in metals or alloys, e.g. $NaAsO_2$ or $NaSbO_2$ may be deposited on the $\beta$-alumina matrix if detection of As or Sb respectively is required. For determination of sulphur, it is necessary to use a relatively high-melting salt such as $CaSO_4$ in contact with Ca/$\beta$-alumina matrix, and for detection of silicon a silicate should be used as the deposition phase. Normally such a salt will be oxidic in character.

By "oxidic" as used herein, there is meant a compound in which the elements are chemically combined with oxygen.

The method according to the invention may be used for on-line detection of minor elements, to monitor the progress of refining or alloying operations carried out on alloy or metal melts.

The invention in another aspect provides a method of measuring the concentration of a minor element in a metal melt, wherein a sensor is immersed in the melt and the EMF (electro-motive force) of the resulting cell is measured.

Preferably the measured EMF is used as a measure of the concentration of the minor element in the melt at constant oxygen concentration.

BRIEF DESCRIPTION OF THE DRAWINGS

The invention will now be described in detail with reference to the accompanying drawings, wherein:

FIG. 6 is a schematic cross-sectional view of an electrolytic sensor in accordance with the invention.

DETAILED DESCRIPTION

Figure 1:
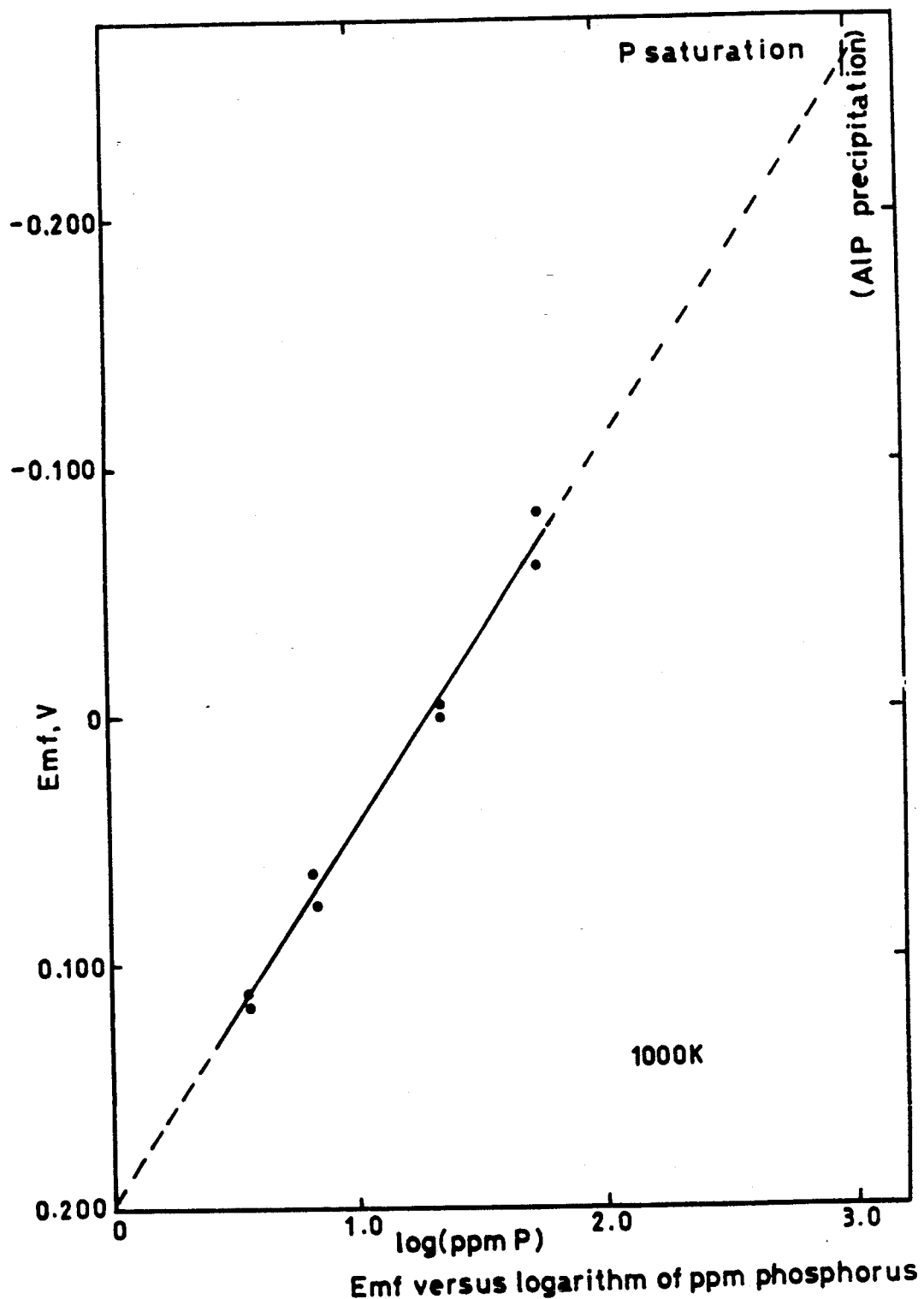
FIGS. 1 to 3 are graphs of EMF plotted against concentration of the element being detected.

An exemplary embodiment of the electrolytic sensor of the invention is shown in FIG. 6, wherein a tubular member 1, which may be alumina, closed at the lower end thereof by solid electrolyte matrix 2 is immersed in molten metallurgical phase 6, an electrode or electrical lead 3 which may be made of iron has one end contacting the solid electrolyte matrix 2 and the other end connected to a voltmeter 7, and an electrical lead 5 having one end immersed in the molten metallurgical phase 6 and the other end connected to voltmeter 7, the immersed end of lead 5 being spaced from solid electrolyte 2. Voltmeter 7 measures the voltage between the two leads 3 and 5 across the electrolyte matrix 2. The lead 5 may be an iron wire. A reference material 4, which may be metal, oxide or carbide and which is electrically conducting, is disposed within the solid electrolyte 2 and the end of conductor 3 extends through reference material 4. The solid electrolyte 2 is preferably based on β-alumina or α+β alumina. A compound 8 comprising the element to be detected and an element whose ions are mobile in the solid electrolyte matrix is deposited on solid electrolyte matrix 2. The element of the compound to be detected is normally a polyvalent non-metallic or semi-metallic element, such as phosphorous, silicon, arsenic, antimony or sulphur, for example. The mobile element of the compound is normally a monovalent or divalent element such as an alkali or alkaline-earth element including Na, Li, K or Ca.

Thus, the solid electrolyte may be in the form of a closed-end tube in which a reference material, usually a mixture of a ferric oxide and a metal ferrite, is placed. The conducting and deposition phases may be platinum/sodium phosphate vapor-deposited on the solid electrolyte matrix tube which contains sodium ions. Iron wires similar to 3 and 5 are inserted into the reference material and into the melt 6 to be tested, the iron wires being connected to a voltmeter, such as shown in 7 in FIG. 6.

The invention will be further illustrated by the following Examples, in which Example 1 relates to the detection and measurement of phosphorus in molten tin, Example 2 to the detection and measurement of phosphorus in aluminum/silicon alloys, Example 3 to the measurement of oxygen and sulphur in molten copper, Example 4 to the measurement of silicon in aluminum, and Example 5 to the measurement of oxygen and sulphur in lead.

An electrolytic sensor for phosphorus detection was prepared as follows:

An isopressed pellet of $Na_3PO_4 + Pt$ was heated by a W-coil to a temperature T of at least 1600° C. within an evacuated chamber and the vapor was allowed to deposit on the outer surface of a β-alumina tube. A reference material (ferric oxide + metal ferrite) was enclosed within the tube. Electrical connections were made via iron wires inserted into the reference material and into the melt to be tested, these being connected via a voltmeter.

EXAMPLE 1
Measurement of Phosphorus in Molten Tin

As phosphorus sensor prepared as described above was immersed in molten tim at 600° C. The EMF obtained with pure (99.999%) tin prior to P additions was 0.62V approximately. This initial attainment of equilibration takes about 20–30 mins. Successive addition of phosphorus in the form of red P led to continuous decrease in the EMF values and an apparent saturation at −0.05V approximately. When oxygen measurements were carried out in conjunction, the EMF's appeared to be independent of P addition, and attained a steady EMF in 60–90 minutes. Experiments at 700° C. improved the response time of both the P and O sensors by 10 and 15 mins. respectively.

The oxygen saturation was observed at 0.968V, while the P saturation occurred at 0.152V.

EXAMPLE 2
Measurement of Phosphorus in Molten Aluminum/Silicon Alloy

Using a phosphorus sensor prepared as described above, tests were carried out on a molten Al/Si alloy containing known amounts of phosphorus. The reaction at the working surface can be represented as:

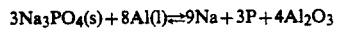

$$3Na_3PO_4(s) + 8Al(l) \rightleftharpoons 9Na + 3P + 4Al_2O_3$$

for the electrolytic cell represented as:

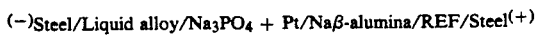

$$(-)Steel/Liquid\ alloy/Na_3PO_4 + Pt/Naβ\text{-alumina}/REF/Steel^{(+)}$$

The relationship between the EMF of this cell and the phosphorus content of the melt can be expressed as:

$$\log[ppmP] = A + B[EMF]$$

where A and B are constants.

A plot of EMF vs. log [ppmP] is shown in FIG. 1. Further phosphorus additions were made to the melt, in the form of $P_2O_5$. Once the EMF reached the value of −0.260 V (±0.015) further additions of $P_2O_5$ gave no change in the EMF value. This is consistent with the attainment of P saturation of the melt and the onset of AlP precipitation, as is predicted by the Al-P phase-diagram.

EXAMPLE 3
Measurement of Oxygen and Sulphur in Molten Copper (a) Oxygen Measurement Molten copper at 1100° C. was saturated with oxygen using $Cu_2O$ and oxygen gas. The following cells were set up to measure the oxygen content of the melt:

| | |
|---|---|
| (−) Fe,FeO/Ca-β-alumina/Cu(l) (+) (O.sat.) | (CELL A) |
| (−) Fe,FeO/Na-β-alumina/Cu(l) (+) (O.sat.) | (CELL B) |

The average EMF readings from these two cells were

| | |
|---|---|
| CELL A | 0.541 V (±0.015V) |
| CELL B | 0.550 V (±0.02V) |

(b) Sulphur Measurement

Sulphur additions were made to the molten copper at 1100° C., using $Cu_2S$ in copper foil. The following cell was set up:

| |
|---|
| (−) Cu(l)/CaSO_4/Ca-β-alumina/Fe,FeO (+) (O.sat) +Cr (with S additions) |

The following EMF values were measured for different sulphur concentrations at constant (saturated) oxygen concentration:

| Wt % S | EMF (mV) |
|---|---|
| 0.0012 | 64 |
| 0.0032 | 12 |
| 0.0066 | −23 |
| 0.0158 | −80 |
| 0.0407 | −149 |
| 0.0631 | −287 |
| 0.1122 | −268 |
| 0.3020 | −272 |

| Wt % S | EMF (mV) |
| --- | --- |
| 0.6050 | −320 |

Figure 2:
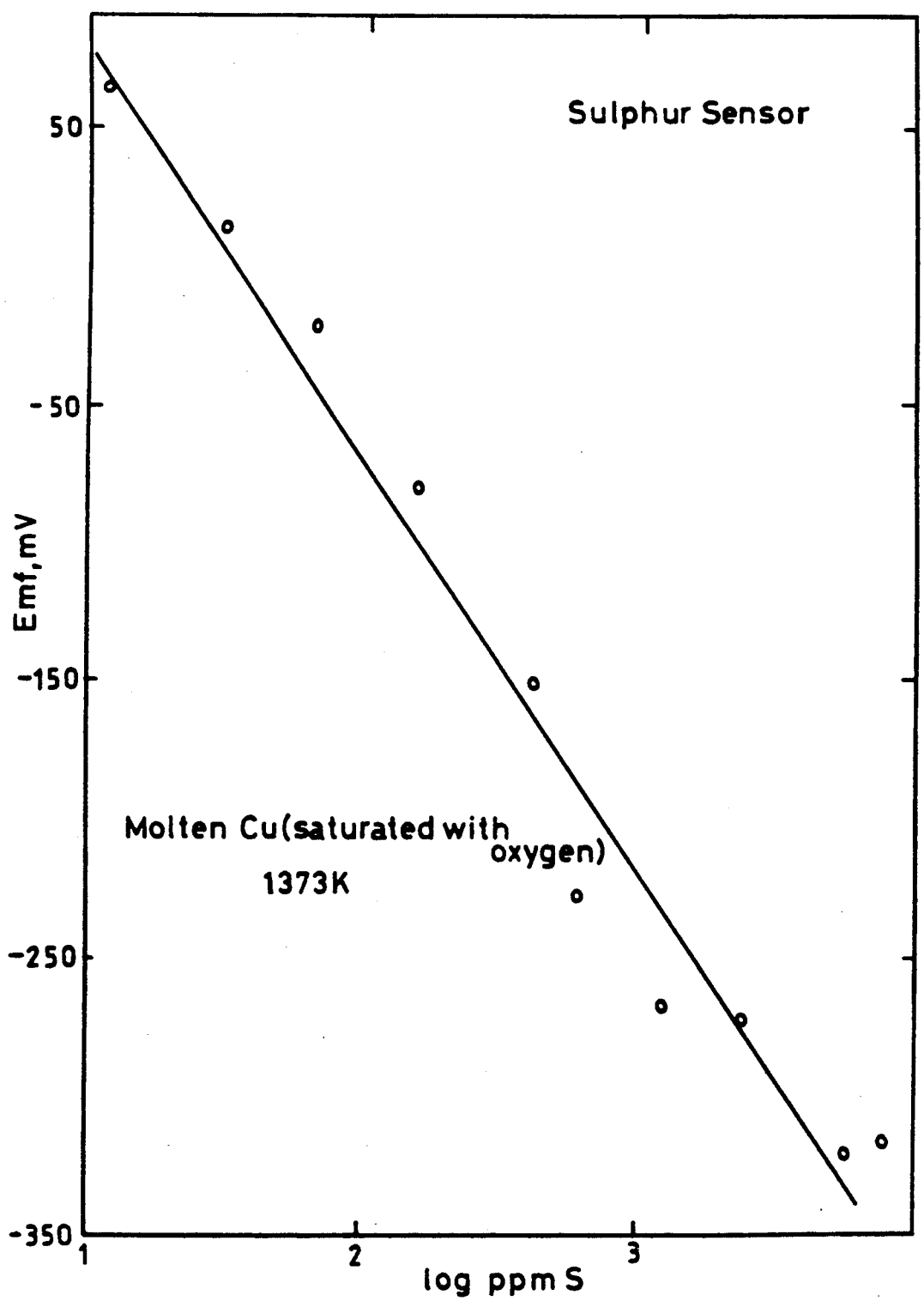

A plot of EMF (mV) vs. log (ppmS) in melt is shown in FIG. 2.

In a second experiment copper at 1100° C. containing 400 ppm oxygen was measured using cells A+B (see above).

The following EMF measurements were obtained:

| CELL A | 0.398 v (±0.025) |
| --- | --- |
| CELL B | 0.411 v (±0.025) |

With added sulphur at the concentrations specified the following EMF values were obtained at constant oxygen concentration:

| Wt % S | Average EMF (V) ±15 mV |
| --- | --- |
| 0.0017 | NO STABLE EMF |
| 0.0199 | 0.464 V. |
| 0.0631 | 0.420 V. |
| 0.1096 | 0.349 V. |
| 0.1995 | 0.322 V. |
| 0.5543 | 0.242 V. |
| 0.6218 | 0.208 V. |

Further sulphur additions had no added effect.

Figure 3:
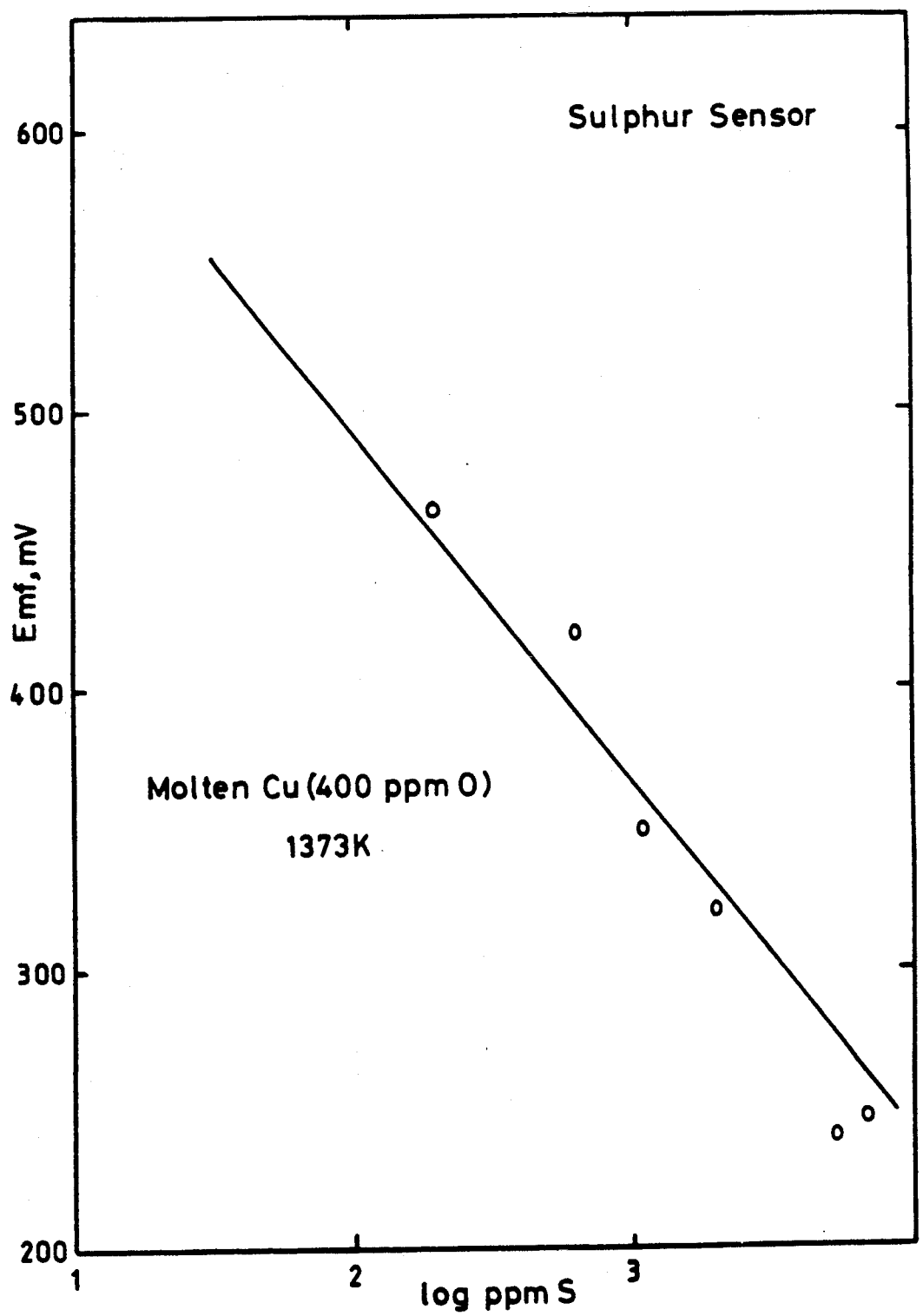

A plot of EMF (mV) vs. log (ppmS) in melt is shown in FIG. 3.

EXAMPLE 4

Measurement of Silicon in Molten Aluminum

The following cell was set up in molten aluminum at 732° C. (+15°)

| (−) Al—Si/2Na$_2$O.SiO$_2$/Na β-alumina/Na$^{(+)}$ +Cr | (REF) |
| --- | --- |

The oxygen content (PO$_2$) was measured using the following cells:

| (−) Al—Si/Ca-β-alumina/Fe,FeO$^{(+)}$ | (CELL A) |
| --- | --- |
| (−) Al—Si/Na-α+β-alumina/Fe,FeO$^{(+)}$ | (CELL B) |

The measured oxygen-dependent EMF'S were as follows:

| CELL A | 1.325 V. (±20 mV) |
| --- | --- |
| CELL B | 1.315 V. (±20 mV) |

These EMF values are independent of silicon additions to the aluminum melt.

With the addition of silicon (as Al/Si alloy in aluminum foil) the following EMF's were obtained.

| Wt % Si | EMF (V) |
| --- | --- |
| 0.1 | −0.145 V |
| 1.0 | −0.410 V |
| 6.0 | −0.731 V |

EXAMPLE 5

Measurement of Oxygen and Sulphur in Molten Lead

The following cells were set up:

| (−)Pb(1)/CaSO$_4$/Ca-β-alumina/Fe,FeO$^{(+)}$ (Saturated with O+S) | (CELL A) |
| --- | --- |
| (+)Pb(1)/Ca-β-alumina/Fe,FeO$^{(−)}$ (O saturated) | (CELL B) |

The following measurements were made:

The CELL B EMF being a measure of oxygen concentration and CELL A EMF being a measure of sulphur concentration.

| T °C. | T °K. | EMF CELL A (mV) | EMF CELL B (mV) |
| --- | --- | --- | --- |
| 590 | 863 | 39 | 405 |
| 615 | 888 | 19 | 412 |
| 655 | 928 | −17 | 417 |
| 701 | 974 | −47 | 427 |
| 749 | 1022 | −86 | 437 |
| 810 | 1083 | −133 | 450 |
| 907 | 1180 | −211 | 467 |

CELL A EMF (mV) = 713.5 − 0.78 T(K)
CELL B EMF (mV) = 236.5 + 0.196 T(K)

Figure 4:
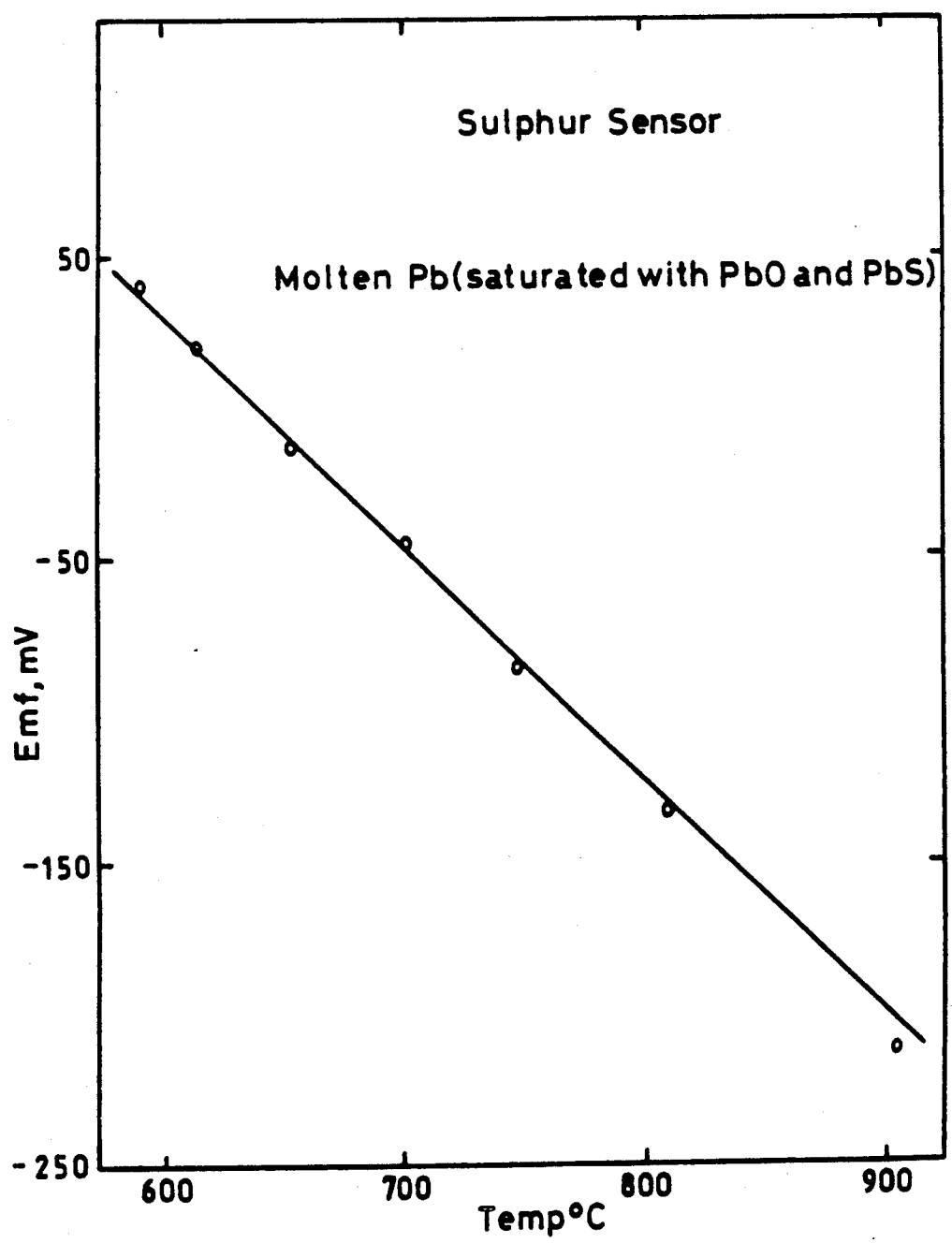
FIGS. 4 and 5 are graphs of EMF plotted against temperature.
Figure 5:
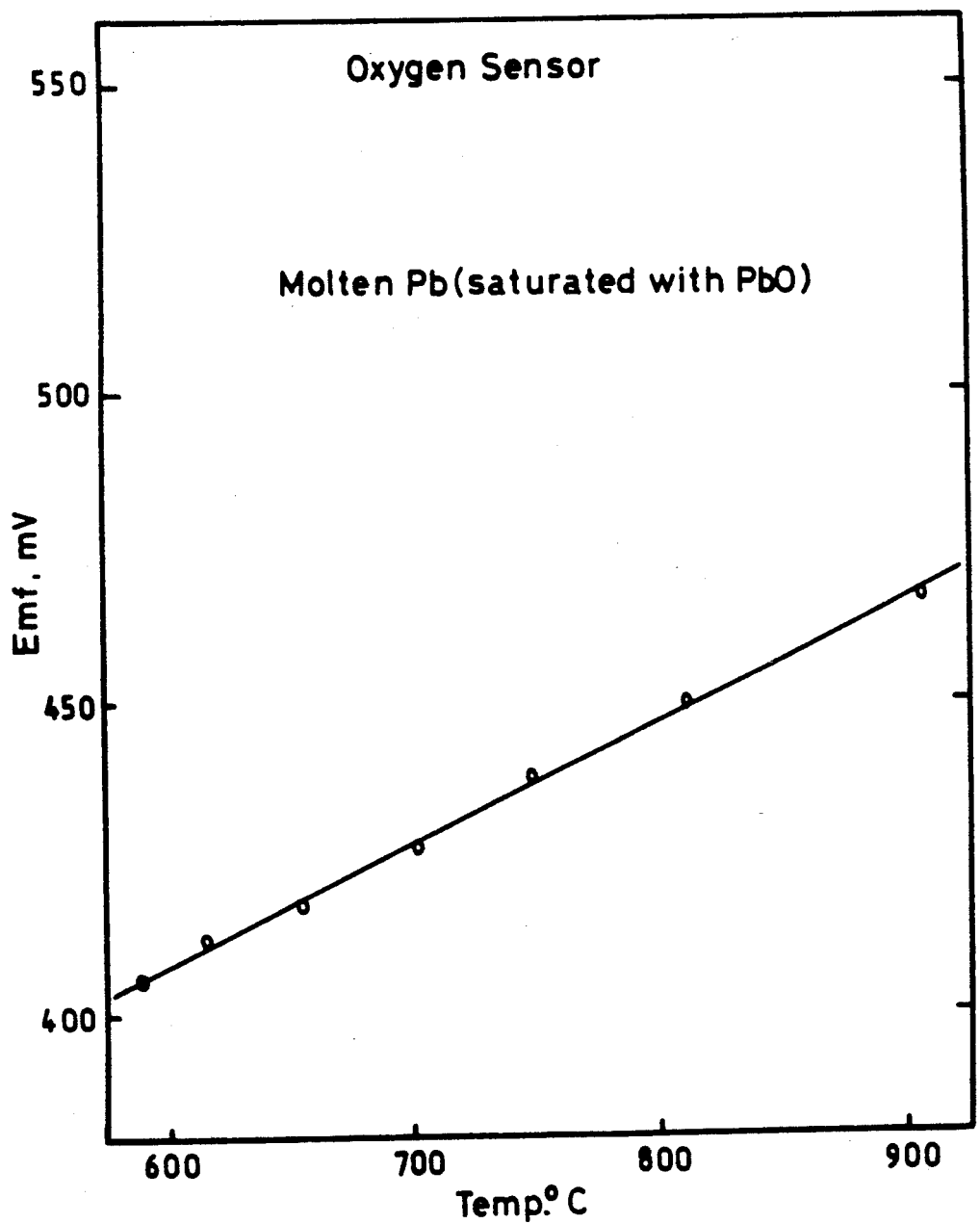

The plots of EMF (mV) vs TEMP (°C.) for CELLS A and B are shown in FIGS. 4 and 5.

We claim:

1. A method for the detection and measurement of a minor element in a molten metal, said minor element being selected from the group consisting of phosphorous, silicon, arsenic, antimony and sulphur comprising:
   immersing a first electrical lead in said molten metal;
   disposing a solid electrolyte in said molten metal in spaced relationship to said first electrical lead, said solid electrolyte comprising a matrix of alumina selected from the group consisting of β-alumina and α+β alumina and including a compound comprising the element to be detected and measured, oxygen, and an element selected from the group consisting of alkali and alkaline earth metal elements, said elements being chemically combined with said oxygen, said compound dissociating into its constituent elements under the condition of measurement in said molten metal;
   connecting a second electrical lead to said solid electrolyte matrix so that said solid electrolyte matrix is between said leads and separates said second lead from said first lead when said first lead and said solid electrolyte matrix are disposed in said molten metal; and
   measuring the EMF between said leads as an indication of the concentration of the minor element in said molten metal.

2. The method as claimed in claim 1 and further comprising:
   depositing a metallic electrical conductor with said compound on said solid electrolyte matrix prior to disposing said solid electrolyte matrix in said molten metal.

3. The method as claimed in claim 2 wherein: said metallic conductor comprises a precious metal.

4. The method as claimed in claim 1 wherein:
said solid electrolyte matrix comprises a $\beta$-alumina tube; and further comprising
providing a coating of $Na_3PO_4$ and platinum on the outer surface of said tube;
enclosing a reference material of ferric oxide and metal ferrite within and in contacting relationship with said tube; and
said first electrical lead comprises an iron wire and said second electrical lead comprises an iron wire inserted into said reference material.

5. A method for the detection and measurement of a minor element in a molten metal, said minor element being selected from the group consisting of phosphorous, silicon, arsenic, antimony and sulphur comprising:
immersing a first electrical lead in said molten metal;
immersing at least part of a tubular member in said molten metal in spaced relationship to said first electrical lead;
providing a closed end on said tubular member immersed in said molten metal, at least said closed end comprising a solid electrolyte matrix of alumina selected from the group consisting of $\beta$-alumina and $\alpha + \beta$ alumina and including a compound comprising the element to be detected and measured, oxygen, and an element selected from the group consisting of alkali and alkaline earth metal elements, said elements being chemically combined with said oxygen, said compound dissociating into its constituent elements under the condition of measurement in said molten metal;
providing a second electrical lead having one end contacting said solid electrolyte matrix so that said solid electrolyte matrix is between and separates said leads when said first lead and said solid electrolyte matrix are immersed in said molten metal; and
measuring the voltage between said first and second electrical leads as an indication of the concentration of said minor element in said molten metal.

6. The method as claimed in claim 5 and further comprising:
depositing a metallic electrical conductor with said compound on said solid electrolyte prior to immersing said solid electrolyte matrix in said molten metal.

7. The method as claimed in claim 6 wherein: said metallic conductor comprises a precious metal.

* * * * *